US010335056B2

(12) United States Patent
Seitz et al.

(10) Patent No.: US 10,335,056 B2
(45) Date of Patent: Jul. 2, 2019

(54) SENSOR FOR ELECTRICALLY MEASURING A FORCE HAVING A SPRING UNIT ARRANGED IN-BETWEEN SURFACES

(71) Applicants: Novel GmbH, Munich (DE); Peter Seitz, Munich (DE)

(72) Inventors: Peter Seitz, Munich (DE); Ahmad Dahrouj, Munich (DE)

(73) Assignees: Novel GmbH, Munich (DE); Peter Seitz, Munich (DE)

( * ) Notice: Subject to any disclaimer, the term of this patent is extended or adjusted under 35 U.S.C. 154(b) by 0 days.

(21) Appl. No.: 15/554,632

(22) PCT Filed: Feb. 22, 2016

(86) PCT No.: PCT/EP2016/053620
§ 371 (c)(1),
(2) Date: Aug. 30, 2017

(87) PCT Pub. No.: WO2016/142156
PCT Pub. Date: Sep. 15, 2016

(65) Prior Publication Data
US 2018/0078176 A1 Mar. 22, 2018

(30) Foreign Application Priority Data
Mar. 6, 2015 (DE) .................. 10 2015 103 261

(51) Int. Cl.
A61B 5/00 (2006.01)
G01L 1/04 (2006.01)
A61B 5/103 (2006.01)
G01L 1/14 (2006.01)

(52) U.S. Cl.
CPC .......... A61B 5/1036 (2013.01); A61B 5/4851 (2013.01); A61B 5/686 (2013.01);
(Continued)

(58) Field of Classification Search
CPC .. A61F 2/70; A61F 2/76; A61F 2/7812; A61F 2/80; A61F 2002/7635;
(Continued)

(56) References Cited

U.S. PATENT DOCUMENTS 2,649,579 A * 8/1953 Alexander ............. G01V 1/208
324/661
3,782,486 A * 1/1974 Kuhn ....................... G01G 7/06
177/210 R (Continued)

FOREIGN PATENT DOCUMENTS

DE 31 13 745 A1 10/1982
DE 34 11 528 A1 10/1985

(Continued)

OTHER PUBLICATIONS

International Preliminary Report on Patentability for Application No. PCT/EP2016/053620, dated Sep. 12, 2017.
(Continued)

Primary Examiner — Brandi N Hopkins
(74) Attorney, Agent, or Firm — Marshall, Gerstein & Borun LLP

(57) ABSTRACT

A sensor for electrically measuring a force distributed unevenly across a measurement surface of the sensor includes a spring device between a measurement surface and a counter-surface. A first measuring element is arranged in or on the measurement surface and a second measuring element is arranged in or on the counter-surface, the elements substantially completely covering these surfaces in each case. The measuring elements include capacitor plates, and are designed such that the measuring signal can be generated from a distance between the measuring elements. The spring device has a large number of elastically designed spring members which are arranged spaced apart from each other by gaps so that each spring member upon loading by the
(Continued)

force can deform into the gaps. This arrangement makes it is possible to measure unevenly distributed forces between bodies which may be of very different forms.

19 Claims, 3 Drawing Sheets

(52) U.S. Cl.
CPC .......... *A61B 5/6807* (2013.01); *A61B 5/6811* (2013.01); *A61B 5/6887* (2013.01); *G01L 1/04* (2013.01); *G01L 1/146* (2013.01); *A61B 5/6804* (2013.01); *A61B 2562/0252* (2013.01)

(58) Field of Classification Search
CPC ... A61F 2002/785; G01L 1/127; G01L 1/146; G01L 5/164; G01L 5/165; A61G 7/057; A61G 2203/32; A61B 5/6892; A61B 5/6894; A61B 5/447; A61B 5/6807; A61B 5/1036; Y10T 29/49099; Y10T 29/49103; G01D 5/2412
See application file for complete search history.

(56) References Cited

U.S. PATENT DOCUMENTS

| | | | | |
|---|---|---|---|---|
| 3,875,481 A * | 4/1975 | Miller | ...................... | G01G 7/06 361/283.1 |
| 4,266,263 A * | 5/1981 | Haberl | ................... | G08B 13/26 177/210 C |
| 6,999,301 B1 * | 2/2006 | Sanftleben | ............... | G01G 7/06 340/438 |
| 7,368,921 B2 * | 5/2008 | Deangelis | ............ | G01D 5/2405 324/661 |
| 7,395,717 B2 * | 7/2008 | DeAngelis | .............. | G01L 1/146 73/724 |
| 7,719,007 B2 * | 5/2010 | Tompkins | ................ | G01L 1/142 257/48 |
| 2016/0015311 A1 * | 1/2016 | Jiang | ......................... | A61F 2/80 623/33 |

FOREIGN PATENT DOCUMENTS

| | | |
|---|---|---|
| DE | 36 34 855 C1 | 3/1988 |
| DE | 196 53 427 A1 | 7/1998 |
| WO | WO-2014/068269 A1 | 5/2014 |

OTHER PUBLICATIONS

Examination Report for German Application No. 10 2015 103 261.9, dated Sep. 9, 2015.
International Search Report and Written Opinion for Application No. PCT/EP2016/053620, dated May 12, 2016.

* cited by examiner

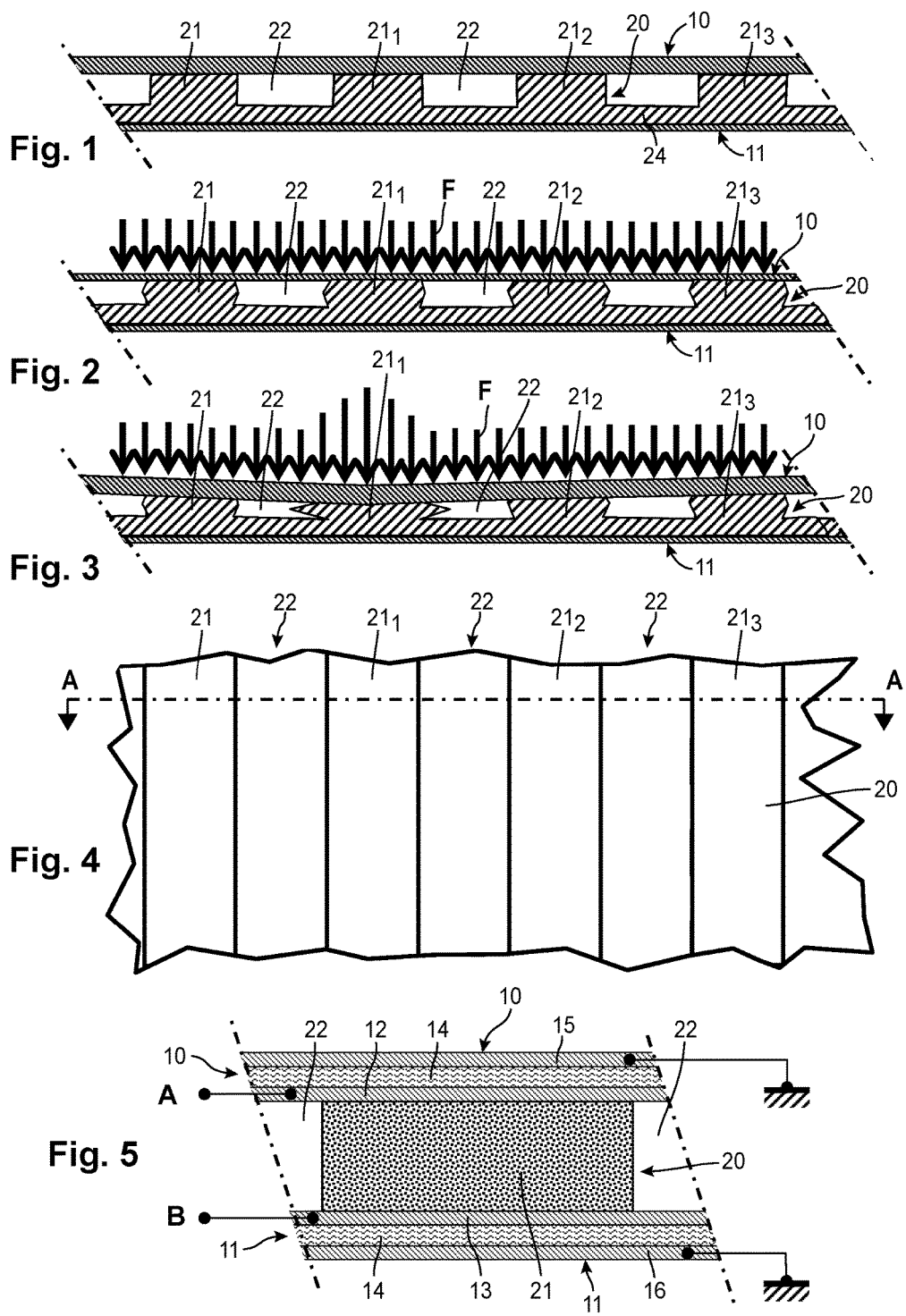

SENSOR FOR ELECTRICALLY MEASURING A FORCE HAVING A SPRING UNIT ARRANGED IN-BETWEEN SURFACES

BACKGROUND

The invention relates to an (individual) sensor for electrically measuring a force acting on the sensor which is distributed unevenly over a measurement surface of the sensor.

Personal scales are suitable for measuring a force acting on them, e.g. a force corresponding to the weight of a user, even if this force is distributed unevenly over the rigid standing surface. Such measurement becomes problematic when it is desired to measure a force applied by a user, e.g. in a shoe. Such measurement is necessary in the case of various medical indications, in particular when the person "monitored" is supposed to perform a specific exercise and has to access the force applied easily.

A capacitive measuring arrangement for determining forces or pressures in which a large number of individual sensors are distributed over a surface, e.g. an insole in a shoe, is known from DE 36 34 855 C1. The sensors in the case of the known arrangement consist of capacitors, i.e. of a large number of capacitor surfaces which are constructed in a matrix and are scanned individually as a matrix. A total force or a total pressure can be calculated from the sum of the individual forces or individual pressures. In this case, it hardly matters whether individual regions of the entire surface are under a greater or lesser load since the total surface is divided into smaller partial surfaces, so that partial forces can be measured and added up. If in the case of this arrangement the acting forces are distributed beyond the measurement surface, i.e. if the total sensor surface is too small, a correct measurement result cannot be derived.

When an elastic sensor (as mentioned above) is required, the measurement results in the case of full-surface sensor elements, e.g. capacitor films, are extremely inaccurate if the force is distributed unevenly.

It is an object of the invention to set forth a sensor of the type referred to first hereinbefore such that a correct total force measurement can be derived in a simple manner.

This object is achieved by a sensor according to claim 1. Particular uses of the sensor are named in claim 12.

In particular, this object is achieved by a sensor for electrically measuring a force (F) acting on the sensor within a specified measuring range, which force is distributed unevenly over a measurement surface (10) of the sensor, wherein an electrical force measurement signal is generated, comprising an areally formed spring device (20) which is arranged between the measurement surface (10) and a counter-surface (11), wherein a first measuring element (12) is arranged in or on the measurement surface (10) and a second measuring element (13) is arranged in or on the counter-surface, the elements substantially completely covering these surfaces in each case, wherein the measurement surface (10) and the counter-surface (11) plus the measuring elements (12, 13) are designed to be elastically deformable, wherein the measuring elements (12, 13), e.g. capacitor plates, are designed such that the measuring signal can be generated from a distance between the measuring elements (12, 13), wherein the spring device (20) has a large number of incompressible but elastically designed spring members (21 to 21*n*) which are arranged spaced apart from each other by gaps (22) in such a way that each spring member (21 to 21*n*) upon loading by the force (F) or a fraction of this force (F) can deform, into the gaps (22) and hence in a space-consuming manner, and wherein each spring member is designed such that its height between the measurement surface and the counter-surface upon loading of the sensor by the force (F) within the specified measuring range is linearly proportional to a partial force acting thereon.

Surprisingly, it has turned out that when the sensor is loaded by forces within a specified measuring range it is not necessary to operate with linearisation "over everything" as with rigid sensors, with which an even distribution of forces onto all the regions of the sensor takes place, regardless of how the effective forces are distributed. Depending on the specified measuring range, then the overall arrangement can be such that the spring members have a linear characteristic within measuring ranges of small area as well. As a result, it is possible to measure a force sum by means of the sensor, namely substantially independently of the distribution of the effective partial forces.

Furthermore, the measurement surface and the counter-surface plus the measuring elements are designed to be deformable, namely in particular elastically deformable. Therefore it is not—as in the case for example of personal scales—rigid surfaces which are used as the measurement surface and counter-surface, but elastically resilient surfaces, so that for example an insole in a shoe can be designed as a sensor. Preferably in this case the measurement surface and/or the counter-surface are designed as a textile material or comprise a textile material, which may be in particular a knitted fabric or a woven fabric. Such materials are known per se. Particularly preferred is an embodiment in which the measuring elements comprise capacitor plates, with a capacitance between the capacitor plates being able to be measured to generate the force measurement signal. The technology necessary for this is already very well developed.

At this point it should be pointed out that the measuring elements may also be constructed as inductors or as ohmic resistors (or mixtures thereof), and that capacitor plates or capacitors as measuring elements are discussed as a preferred example of embodiment in the following description.

The measurement surface and/or the counter-surface are connected to the spring members by fastening means. These fastening means may be designed in diverse ways. What is important in this case is however that the measurement surface and the counter-surface be connected to the spring members such that the geometric overall arrangement remains substantially constant. In this case, the fastening means are preferably designed elastically such that the measurement surface and/or the counter-surface is/are elastically displaceable relative to the spring devices. This is necessary in particular when curving of the measurement surface or of the counter-surface occurs. Fastening means which are displaceable in such a manner may for example be elastic bonded joints.

The measurement surface and the counter-surface preferably have in addition to the first or second measuring element respectively, on their sides remote from the spring device, shielding elements for electrically shielding the measuring elements. As a result, even relatively small measuring signals can be detected with little disturbance.

The spring members may be constructed as geometric bodies in various ways. They may comprise bar-shaped, frusto-pyramidal or frusto-conical individual elements, "frusto-pyramidal" or "frusto-conical" also being taken to mean cuboids or cylinders with very slight angling. These individual elements are arranged at regular distances from each other. In particular silicone rubber is a suitable material here, with Shore hardnesses of 45-55, in particular 47-53, being preferred. Adaptation to the forces to be measured may of course be carried out here.

The spring members may—as described above—be connected together by a bonded joint, or alternatively by a carrier surface from which the individual spring members protrude either on one side or on both sides (with the carrier surface in the middle). In both cases, production of the sensor is particularly simple and precise when the carrier surface is designed in one piece with the spring members.

If the measuring elements comprise capacitor plates, preferably a capacitance measuring device is provided which is connected to the shielding elements and the capacitor plates and is designed such that capacitances between the capacitor plates and the shielding elements can be measured. Since—in a manner known per se—all the capacitor plates and also the shielding means are separated from one another by dielectrics, a measuring signal can be generated herefrom which corresponds substantially to the temperature-dependent material properties of the dielectrics, i.e. in particular the material-dependent and temperature-dependent dielectric constant. By means of this measuring signal, the force measurement signal can be corrected with respect to its temperature dependency in a correction device.

Many different combinations of form and material which permit the aforementioned linearisation are conceivable for the spring elements. In one embodiment, the spring members are assembled from spring members of different geometric construction in groups of spring members which in each case have different spring characteristics from each other, such that they compensate for each other and bring about linearisation of the overall spring characteristic of the group.

A sensor of the type shown here can advantageously be used for a large number of measurement tasks. In particular, these are those measurement tasks in which the surfaces between which the forces occur are curved or—and this is even more difficult with regard to the sensors to be selected—variable during the course of the measurement. In particular, they are in this case measurements of loads exerted by human limbs or effectors of a robot on a surrounding object, e.g. a shoe, a prosthesis, an orthosis, a handle, a steering wheel or a natural or artificial joint, and also tools or workpieces. These can also be taken to mean forces exerted by body parts on subjacent supporting structures, e.g. a car seat, a mattress, a lounger or a riding saddle.

BRIEF DESCRIPTION OF THE DRAWINGS

Below, preferred embodiments of the invention will be illustrated in greater detail with reference to schematic drawings. Therein FIG. 1 is a partial cross-section through a first embodiment of the invention, FIG. 2 is a representation of the arrangement of FIG. 1 upon loading with an even force, FIG. 3 is a representation of the loading of an arrangement according to FIG. 1 with an uneven force, FIG. 4 is a top view of the arrangements of FIGS. 1-3, omitting the measurement surface, with the dot-dash line A-A corresponding to the sections of FIGS. 1-3, FIG. 5 is a more detailed partial section through a further embodiment of the invention.

DETAILED DESCRIPTION

Figure 6:
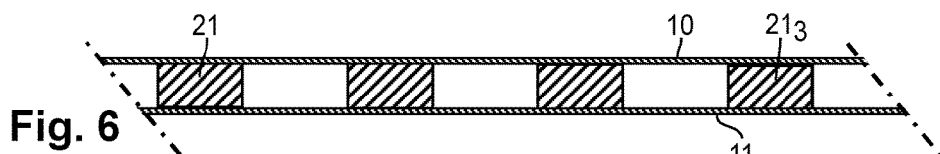
FIG. 6 is a section similar to that of FIG. 1, but through an arrangement according to FIG. 5.

In the following description, the same reference numerals are used for identical parts and for parts which have the same effect.

According to FIG. 1, the sensor comprises a measurement surface 10 and a counter-surface 11, with spring devices 20 being provided between the measurement surfaces 10 and 11. These spring devices 20 comprise spring members 21, $21_1$, $21_2$ and $21_3$ which are connected together via a carrier surface 24. The spring members 21 . . . are formed in one piece with the carrier surface 24 from silicone rubber.

If then a force F, as shown in FIG. 2, acts on the measurement surface 10, the spring members $21_1$ to $21_3$ deform, and therefore expand into gaps 22 which are provided between the bodies $21_1$ to $21_3$.

If the acting force F is distributed unevenly over the measurement surface 10, as is shown in FIG. 3, individual spring members $21_1$ will deform more greatly than the adjacent spring members 21 and $21_2$, with the measurement surface 10 being deformed at the same time. It is therefore important for the measurement surface 10 and generally also the counter-surface 11 to be elastically deformable.

The spring device 20 shown in FIGS. 1-3 consists—as shown in FIG. 4—of bars. This is a particularly simple "basic form".

In the arrangement shown in FIG. 5, a single spring member 21 which is designed substantially as a cuboid is provided. This spring member 21 is covered on both sides with measuring elements or electrodes 12 and 13. Between the electrodes 12 and 13 and outer shielding elements 15, 16 there is provided a dielectric 14. The overall arrangement, i.e. the measurement surfaces 10, 11, consisting of the measuring elements 12, 13, the shielding elements 15, 16 and the dielectric 14, is designed to be elastically deformable, so that deformation can take place as shown in FIG. 3.

Since the capacitance of the spring members 21 arranged between the measuring elements or electrodes 12, 13 is temperature-dependent with regard to its dielectric constant, it is advantageous if this temperature dependency can be compensated. To this end, in multiplex operation the measuring points A and B are connected in parallel and the capacitance between the electrodes 12, 13 (which are connected in parallel) and the shielding elements 15, 16 is measured alternately to the capacitance between the measuring points A and B, i.e. between the electrodes 12 and 13.

From these measurements, a correction signal can be ascertained which can make the capacitance between the measuring elements or electrodes 12, 13 respectively substantially independent of the temperature of the overall arrangement. The electrical circuit necessary for this is not shown separately, since it is in principle familiar to the person skilled in the art who is active in this field.

FIG. 6 once again shows an arrangement corresponding to that of FIG. 5. In this case, the spring members 21 to 21$_3$ are connected directly to the measurement surface 10 or the counter-surface 11, which can be done e.g. by gluing. If the adhesive layer is elastic, this is advantageous when curving or sagging of the overall arrangement occurs.

Figure 7:
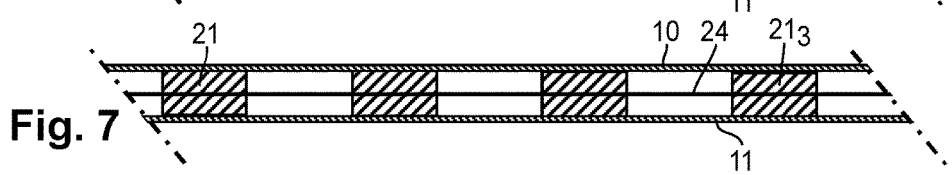
FIG. 7 is a section corresponding to that of FIGS. 1 and 6 through a further embodiment of the invention.

In the arrangement of FIG. 7, the spring members 21 to 21$_3$ are arranged on either side of a carrier surface 24, so that a very symmetrical arrangement is produced.

Figure 8:
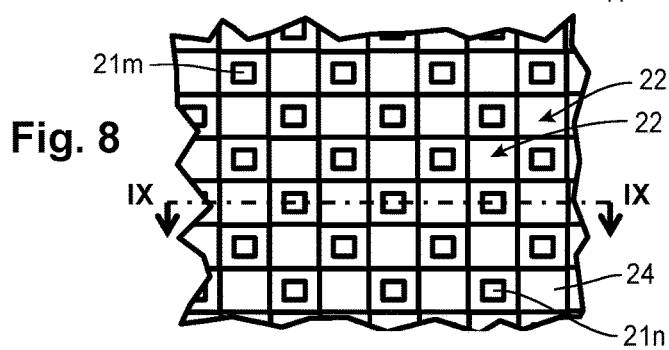
FIG. 8 is a top view of a further embodiment of the invention.
Figure 9:
FIG. 9 is a section along the line IX-IX of FIG. 8.

In the arrangement of FIG. 8, the spring members 21$_m$ to 21$_n$ are designed to be frusto-pyramidal, as is shown in FIG. 9. In this case, the arrangement is such that it is possible for the spring members 21$_m$ to 21$_n$ to yield sideways.

Figure 10:
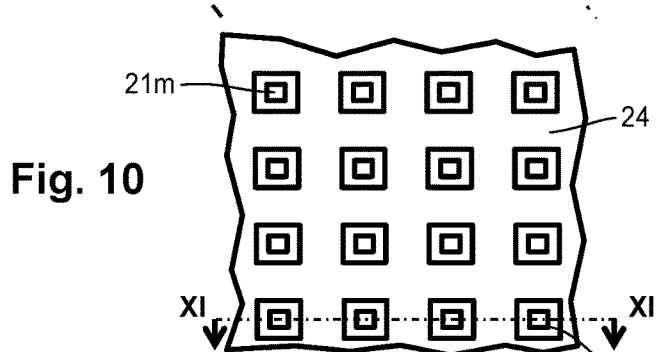
FIG. 10 is a top view of a further embodiment of the invention.
Figure 11:
FIG. 11 is a section along the line XI-XI of FIG. 10.

The arrangement of FIGS. 10 and 11 differs from that of FIG. 8 by a larger grid pattern of spring members 21$_m$ to 21$_n$.

Figure 12:
FIG. 12 is a top view of a further embodiment of the invention.
Figure 13:
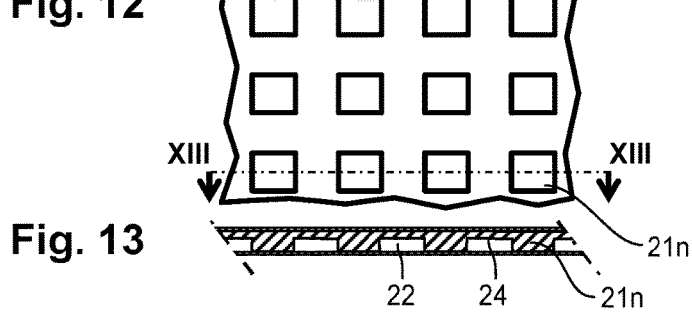
FIG. 13 is a section along the line XIII-XIII of FIG. 12.

The arrangement of FIGS. 12 and 13 corresponds to that of FIG. 10, but with the angle of the truncated pyramids to the carrier surface 24 being substantially 90°.

Figure 14:
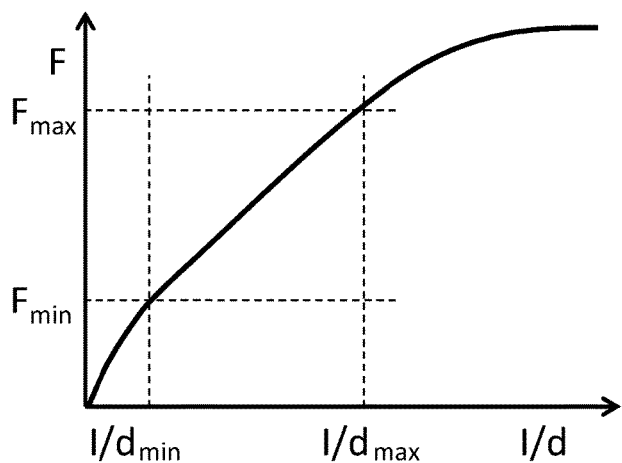
FIG. 14 is a graph by way of example showing a linear range of the spring device.

The forming of the spring members 21 to 21$_n$ mentioned first hereinbefore results in a spring characteristic in accordance with FIG. 14. Within a measuring range between a minimum force Fmin and a maximum force Fmax the change in form, i.e. the change in height d (see FIG. 15) of the spring members 21 to 21$_n$ between a value 1/dmin and a value 1/dmax, runs substantially linearly. Depending on the requirement, i.e. depending on the measurement task, the geometric form and size and also the material are determined such that measurements in the linear range according to FIG. 14 are made possible.

Figure 15:
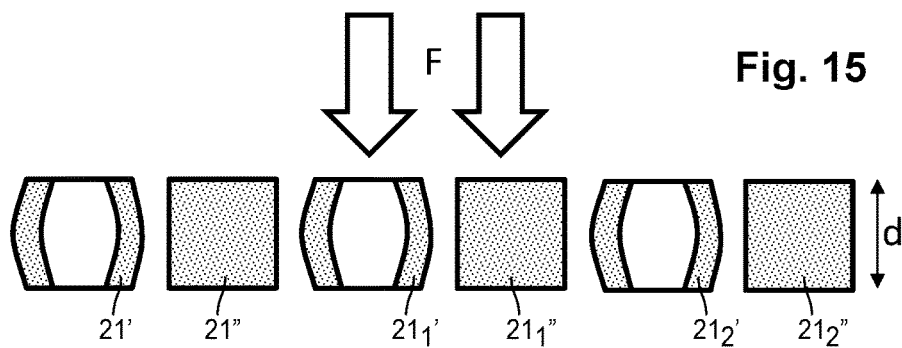
FIG. 15 is a schematic cross-sectional representation of groups of spring members.
Figure 16:
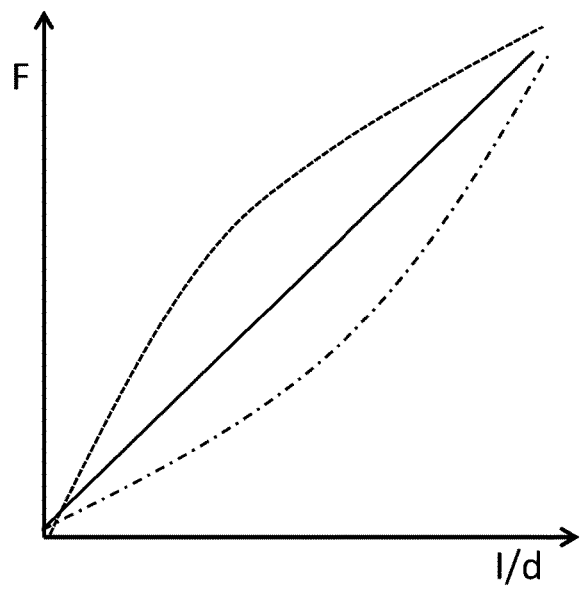
FIG. 16 is a graph corresponding to that of FIG. 15 explaining the spring characteristic of an arrangement according to FIG. 15.

One possible way of linearising spring members consists in dividing them into groups 21', 21"; 21$_1$', 21$_1$", 21$_2$', 21$_2$", the various members 21' and 21" . . . being of geometrically different forms and having different spring characteristics (i.e. ratio d/F), as shown in FIG. 16. The spring member 21' shown in FIG. 15 is based on bulging of the spring member walls, so that with increasing deformation the force necessary for this decreases, whereas in the case of the "solid" spring member 21" the force increases. When added together, the two non-linear curves thereby compensate for each other. It is of course possible to have a large number of different combinations of spring members cooperate here.

LIST OF REFERENCE NUMERALS

10 measurement surface
11 counter-surface
12 first measuring element/electrode
13 second measuring element/electrode
14 dielectric
15 first shielding element
16 second shielding element
20 spring device
21 to 21$n$ spring members
22 gap
24 carrier surface

The invention claimed is:

1. A sensor for electrically measuring a force acting on the sensor within a specified measuring range, which force is distributed unevenly over a measurement surface of the sensor, wherein an electrical force measurement signal is generated, comprising:
   a spring device which is arranged between the measurement surface and a counter-surface,
   a first measuring element arranged in or on the measurement surface and a second measuring element is arranged in or on the counter-surface, the first and second measuring elements comprising capacitor plates covering these surfaces,
   wherein the measurement surface and the counter-surface plus the measuring elements are elastically deformable,
   wherein the measuring elements generate a measuring signal from a distance between the measuring elements,
   wherein the spring device has a large number of incompressible but elastically designed spring members which are arranged spaced apart from each other by gaps, wherein each spring member upon loading by the force or a fraction of this force can deform, into the gaps and hence in a space-consuming manner,
   wherein the height for each spring member between the measurement surface and the counter-surface upon loading of the sensor by the force within the specified measuring range is linearly proportional to a partial force acting thereon,
   wherein the measurement surface and the counter-surface further include shielding elements for electrically shielding the first and second measuring elements, the shielding elements being separated from the capacitor plates of the first and second measuring elements by a dielectric, and
   further including a capacitance measuring device connected to the shielding elements and to the capacitor plates of the first and second measuring elements to measure the capacitances between the shielding elements and the capacitor plates to obtain a temperature signal to be used to correct the measuring signal.

2. The sensor according to claim 1, wherein the measurement surface and/or the counter-surface comprise textile material, in particular a knitted fabric or a woven fabric.

3. The sensor according to claim 2, wherein the measuring elements comprise capacitor plates, with a capacitance between the capacitor plates being able to be measured to generate the force measurement signal.

4. The sensor according to claim 2, wherein the measurement surface and/or the counter-surface are connected to the spring members by fastening means.

5. The sensor according to claim 1, wherein the capacitance between the capacitor plates is able to be measured to generate the force measurement signal.

6. The sensor according to claim 5, wherein the measurement surface and/or the counter-surface are connected to the spring members by fastening means.

7. The sensor according to claim 1, wherein the measurement surface and/or the counter-surface are connected to the spring members by fastening means.

8. The sensor according to claim 7, wherein the fastening means are designed elastically such that the measurement surface and/or the counter-surface is/are displaceable relative to the spring device.

9. The sensor according to claim 1, wherein the shielding elements are disposed on the sides of the measurement surface and the counter-surface remote from the spring device.

10. The sensor according to claim 1, wherein the spring members are arranged at regular distances from each other.

11. The sensor according to claim 10, wherein the spring members are bar-shaped, frusto-pyramidal, or frusto-conical individual elements.

12. The sensor according to claim 10, wherein the spring members are manufactured from silicone rubber.

13. The sensor according to claim 12, wherein the silicone rubber has a Shore hardness between 45 A and 55 A.

14. The sensor according to claim 13, wherein the Shore hardness is between 47 A and 53 A.

15. The sensor according to claim 1, wherein the spring members are connected together via at least one carrier surface.

16. The sensor according to claim 15, wherein the carrier surface is designed in one piece with the spring members.

17. The sensor according to claim 1, wherein one of the spring members comprises a group of spring members wherein the spring members in the group have a spring characteristics which are inverse to one another, to thereby compensate for each other and bring about linearisation of a group spring characteristic.

18. Use of a sensor according to claim 1 for measuring loads exerted by human limbs or effectors of a robot on a surrounding object.

19. Use of a sensor according to claim 18, wherein the surrounding object is a shoe, a prosthesis, an orthosis, a handle, a steering wheel, a natural or an artificial joint, a tool or a workpiece.

* * * * *